(12) United States Patent
Hill

(10) Patent No.: US 9,299,262 B2
(45) Date of Patent: *Mar. 29, 2016

(54) MULTI-EVENT TIME AND DATA TRACKING DEVICE (FOR BEHAVIOR ANALYSIS)

(71) Applicant: Roxanne Hill, Tappan, NY (US)

(72) Inventor: Roxanne Hill, Tappan, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/742,652

(22) Filed: Jun. 17, 2015

(65) Prior Publication Data

US 2015/0287328 A1   Oct. 8, 2015

Related U.S. Application Data

(63) Continuation-in-part of application No. 14/138,000, filed on Dec. 20, 2013, now Pat. No. 9,092,014.

(51) Int. Cl.
| | |
|---|---|
| *G09B 19/00* | (2006.01) |
| *G09B 5/00* | (2006.01) |
| *G06F 3/0484* | (2013.01) |
| *G06F 3/0482* | (2013.01) |
| *G06F 3/0488* | (2013.01) |
| *G04G 11/00* | (2006.01) |
| *G04G 13/02* | (2006.01) |
| *G04B 47/00* | (2006.01) |
| *A61B 5/00* | (2006.01) |
| *G04F 1/00* | (2006.01) |
| *G06F 19/00* | (2011.01) |

(52) U.S. Cl.
CPC *G09B 5/00* (2013.01); *G04B 47/00* (2013.01); *G04G 11/00* (2013.01); *G04G 13/026* (2013.01); *G06F 3/0482* (2013.01); *G06F 3/0484* (2013.01); *G06F 3/04883* (2013.01); *A61B 5/00* (2013.01); *G04F 1/005* (2013.01); *G06F 19/32* (2013.01); *G09B 19/00* (2013.01)

(58) Field of Classification Search
CPC ........ G09B 5/00; G09B 19/00; G06G 13/026; G06G 11/00; G04B 7/00; G06F 3/0482; G06F 3/0484; G06F 3/04883
See application file for complete search history.

(56) References Cited

U.S. PATENT DOCUMENTS

| | | | | |
|---|---|---|---|---|
| 4,012,852 A | * | 3/1977 | Journot | G09B 19/04 434/185 |
| 5,691,932 A | * | 11/1997 | Reiner | G06F 15/025 340/309.4 |
| 5,908,301 A | * | 6/1999 | Lutz | G09B 5/02 128/921 |
| 6,314,405 B1 | * | 11/2001 | Richardson | A61B 5/0002 600/300 |
| 9,092,014 B2 | * | 7/2015 | Hill | G04G 13/026 |
| 2003/0087219 A1 | * | 5/2003 | Berger | G09B 5/00 434/118 |
| 2004/0001022 A1 | * | 1/2004 | Silzer, Jr. | A63B 71/06 343/702 |

(Continued)

*Primary Examiner* — Michael Grant

(57) ABSTRACT

A battery operated multi-event data and time tracking device for monitoring behaviors and behavior-related data for the purpose of analysis, comprising a plurality of buttons on the face and/or touch screen of a device, grouped together and labeled with numbers 1-26 and letters A-Z organized in a qwerty format icons and with icons representing various behavioral events and behavior-related data. The information screen will additionally display various temporal, numerical and anecdotal data corresponding to particular behavioral events. There is also a decimal point button, a clear button and scanning buttons as well as set, data and off switches. The device further comprises a microprocessor, a USB port, a SD card port, wireless, including but not limited to Bluetooth and WiFi capability for data transfer to and from a permanent memory storage or data cloud, wherein data will be organized in graphic format for the analysis of behaviors and behavioral data.

6 Claims, 3 Drawing Sheets

(56) References Cited

U.S. PATENT DOCUMENTS

| | | | | |
|---|---|---|---|---|
| 2005/0283327 A1* | 12/2005 | Bowman | ............ | G06F 19/3475 702/81 |
| 2006/0046238 A1* | 3/2006 | DeGregory | ............ | G09B 7/02 434/350 |
| 2009/0036828 A1* | 2/2009 | Hansen | ............ | G06F 19/3406 604/66 |
| 2009/0181352 A1* | 7/2009 | Hood | ............ | G09B 5/04 434/309 |
| 2012/0075192 A1* | 3/2012 | Marsden | ............ | G06F 3/04886 345/168 |
| 2013/0143186 A1* | 6/2013 | Singletary | ............ | G09B 19/00 434/236 |
| 2013/0309642 A1* | 11/2013 | Singletary | ............ | G09B 19/00 434/236 |
| 2014/0106312 A1* | 4/2014 | Klein | ............ | G06F 19/3475 434/127 |
| 2014/0198623 A1* | 7/2014 | Hill | ............ | G04G 13/026 368/10 |
| 2015/0040069 A1* | 2/2015 | Gunaratnam | ............ | G06F 3/04817 715/834 |

* cited by examiner

MULTI-EVENT TIME AND DATA TRACKING DEVICE (FOR BEHAVIOR ANALYSIS)

CROSS-REFERENCE TO RELATED APPLICATIONS

This nonprovisional patent application is a continuation-in-part of U.S. patent application Ser. No. 14/138,000 entitled Multi-Event Time and Data Tracking filed on Dec. 20, 2013.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

This disclosure is related to the general field of time and data recording, storage, retrieval, organization and transfer, particularly related to the analysis of behaviors. This device is a direct-entry information collection, storage and retrieval device that provides a means to collect, store, organize, analyze, transfer and graphically display relevant behavioral event and program information as well as to provide alarm reminders at specific times or time intervals for selected events or behaviors.

The CDC estimates that currently 1:68 children and 1:42 boys are identified with autism spectrum disorder (ASD) and that in 2008 it was estimated that 1:6 children had been diagnosed with some type of developmental disability. (cdc.gov/ncbddd/autism/data.html) With the incidence of ASD and developmental disabilities on the rise, there has been a growing need for effective treatment methods. Applied Behavior Analysis (ABA) is an empirically validated method of treatment for children and adults with autism and related disorders which has been endorsed by many organizations including the American Academy of Neurology, the American Psychological Association, the American Academy of Pediatrics and the National Institute of Mental Health. (appliedbheaviorcenter.com/aba-endorsements/). In addition, a mental health report released by the United States Attorney General stated that "thirty years of research [has] demonstrated the efficacy of applied behavior methods in reducing inappropriate behavior and in increasing communication, learning and appropriate social behavior." (appliedbheaviorcenter.com/aba-endorsements/).

When using ABA methodology, accurate data collection is critical to obtaining valid data for the analyses used to successfully treat individuals with behavioral challenges. Data collection is typically recorded in a written format on data sheets as it occurs during a treatment session and then is subsequently graphed and analyzed. It can be difficult for behaviorists to remember and accurately record data on paper in a fast-paced program. It can also be distracting to the student when the teacher interrupts treatment after each opportunity to write down data. Furthermore, it can be cumbersome for a behaviorist to carry a pencil, paper and a timing device with them at all times. Finally, the written method leaves all the organization of the information up to the behaviorist, which requires even more time and attention and allows for a greater possibility of human error when transferring data.

Recently, there has been an emergence of computer programs and applications which record, transfer, organize and analyze ABA-related data in much the same way the present invention does. However, these programs are usually dependent on the use of a personal computer device, such as a tablet or smart phone, and would subject the user to much of the same difficulties described in the cross-referenced patent application Ser. No. 14/138,000, specifically in reference to baby behavior tracking applications on smart phones used by parents.

Without a dedicated device for data collection, transfer, organization and analysis in computer-based ABA programs, applications must be accessed through personal computing devices. For a number of reasons, the present invention is more practical than using personal computing devices to record, transfer, organize and analyze behavioral data.

First, personal computing devices usually have a myriad of professional and personal uses. They are often transported between users and locations which can make them susceptible to accidental damage particularly because the screen of a computer tablet (the preferred device used in home and school computer-based ABA programs) is delicate and can be easily scratched or cracked. It is probably more likely for this to occur when behaviorists are handling maladaptive and aggressive behaviors. However, the construction of the present behavior tracking device is much sturdier than most computer tablets with a significantly smaller screen that is surrounded and protected by several inches of plastic around each of its sides thus reducing the risk of damage to the device if inadvertently dropped.

Second, the tablet's size can be cumbersome for a teacher to physically manipulate when recording data during a treatment session. This is especially true when working with younger children, with whom the teacher usually sits in small chairs or on the floor at small desks with them. The tablet would occupy considerable workspace on the child's desk and would have to be placed on the teacher's lap or on the floor next to the teacher, again making the device prone to accidental damage. This problem is essentially eliminated when using the present invention which is palm-sized, inconspicuous and has a convenient clip, which can convert to a stand and can easily be fastened to fabric to be worn around the user's neck or wrist.

Third, using a tablet to track behavior and record data can be quite distracting to students, particularly for those with autism and developmental disabilities, who often have difficulty blocking out peripheral stimuli. A tablet could easily divert a student's attention when a teacher uses it to record data, especially when that tablet is also used as reinforcement or for other program activities.

Fourth, since it has become quite common for behaviorists to use applications on computer tablets not only as reinforcement during a treatment session but also to conduct program-related activities, when the tablet is being used in one of these ways, it prohibits the behaviorist from taking data on those particular activities or behaviors.

Fifth, operating the tablet during a treatment session can be awkward and time-consuming for a teacher, who must access the application again after each time it is used for a program activity or as reinforcement. Then, within the program itself, the teacher must navigate between screens to record data for different programs and behaviors. In spending time to access different functions of the tablet, the teacher may miss or forget important data, especially if the student is engaging in maladaptive behaviors that may be occurring rapidly. In the present device, almost every function that would be used in a treatment session can be accessed on the face of the device requiring little or no navigation.

BRIEF SUMMARY OF THE INVENTION

The present invention discloses an electronic device for tracking, storing, organizing, transferring and analyzing qualitative and quantitative behavior-related data including but not limited to time, duration, frequency, quantity. Its intuitive design allows for the direct-entry collection, storage, retrieval, organization, transfer and analysis of information to and from other computing devices and has the capability to be synched or interfaced with a personal computing device, a main computer and/or a data cloud so it can be further programmed, organized, analyzed and graphically represented.

The collected information can be retrieved from the device itself for a period of time, through the device's memory or optionally through use of an SD card. It can then be downloaded via USB and/or wireless (i.e. Bluetooth and WiFi) transfer to a computer, information cloud, tablet or phone through an application which will organize the information into charts/graphs/tables which can be reviewed, organized, printed and emailed. Information from a computing device or data cloud can also be transferred to the device which might be especially helpful when programming the device for multiple programs and users.

The electronic device comprises a backlit information screen with numbers, letters and various behavior-related and data recording buttons and switches labeled with words or universal symbols that correspond to information on the screen and facilitate easy and direct-entry input. The electronic device is a battery-operated device with a durable clip on the back which a user can adjust to prop up the device on a table or flat surface, wear on the user's belt and/or fasten a comfortable cord/fabric to the device so that it can worn around a user's neck or wrist to maximize portability.

DETAILED DESCRIPTION OF THE INVENTION

Figure 1:
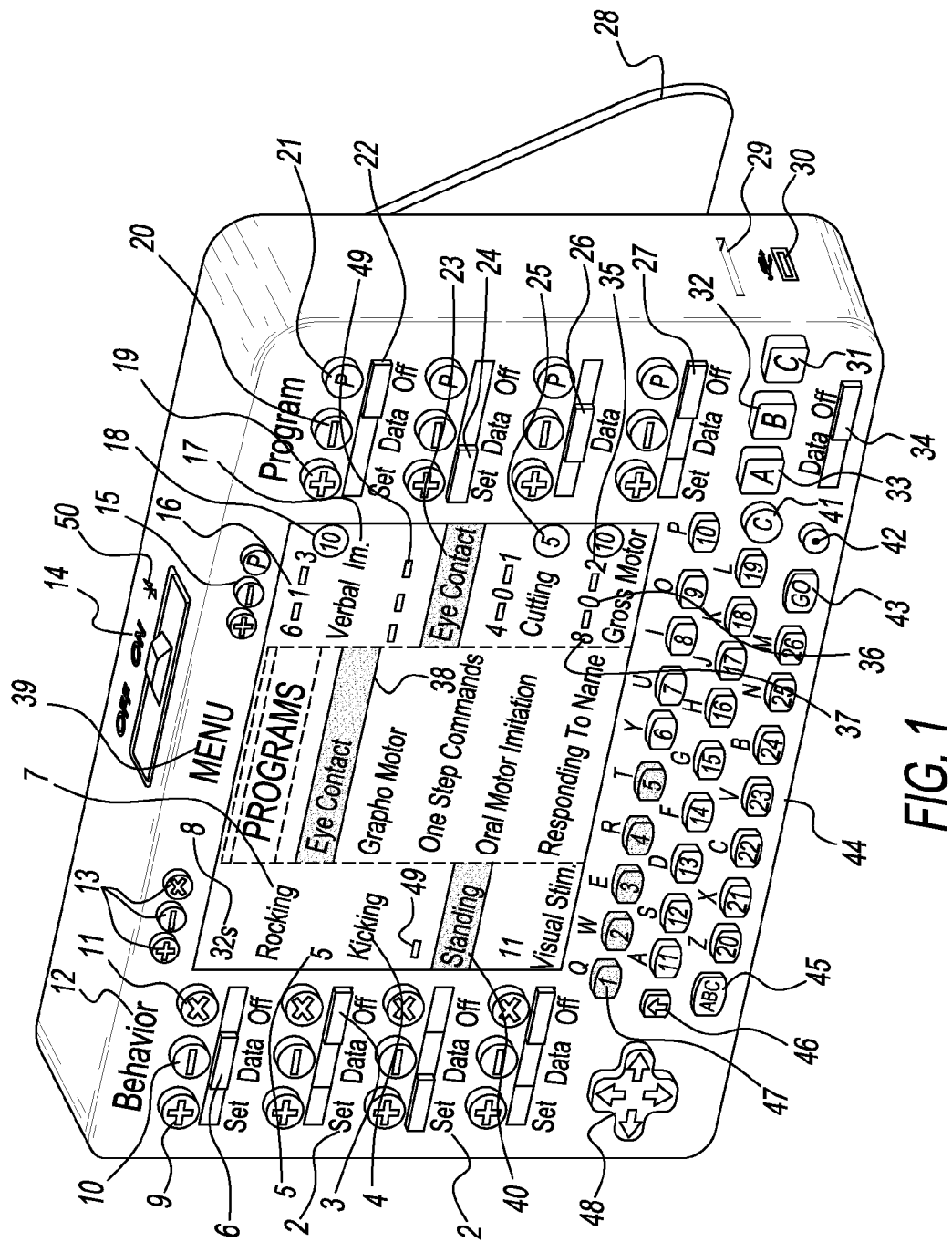
FIG. 1 illustrates a perspective view of the preferred embodiment of the present invention.

Hereinafter, selected examples and operating functions of a multi-event time and data tracking device dedicated to the applied analysis of behaviors will be discussed in the following with reference to the accompanying drawings FIG. 1, FIG. 2 and FIG. 3. It will be appreciated by those skilled in the art that the following discussion is for illustration purposes only and should not be interpreted in limitation of the invention. Other variances within the scope of this disclosure are also applicable.

"Optional" or "optionally" means that the subsequently described circumstance may or may not occur, so that the description includes instances where the circumstance occurs and instances where it does not.

Figure 3:
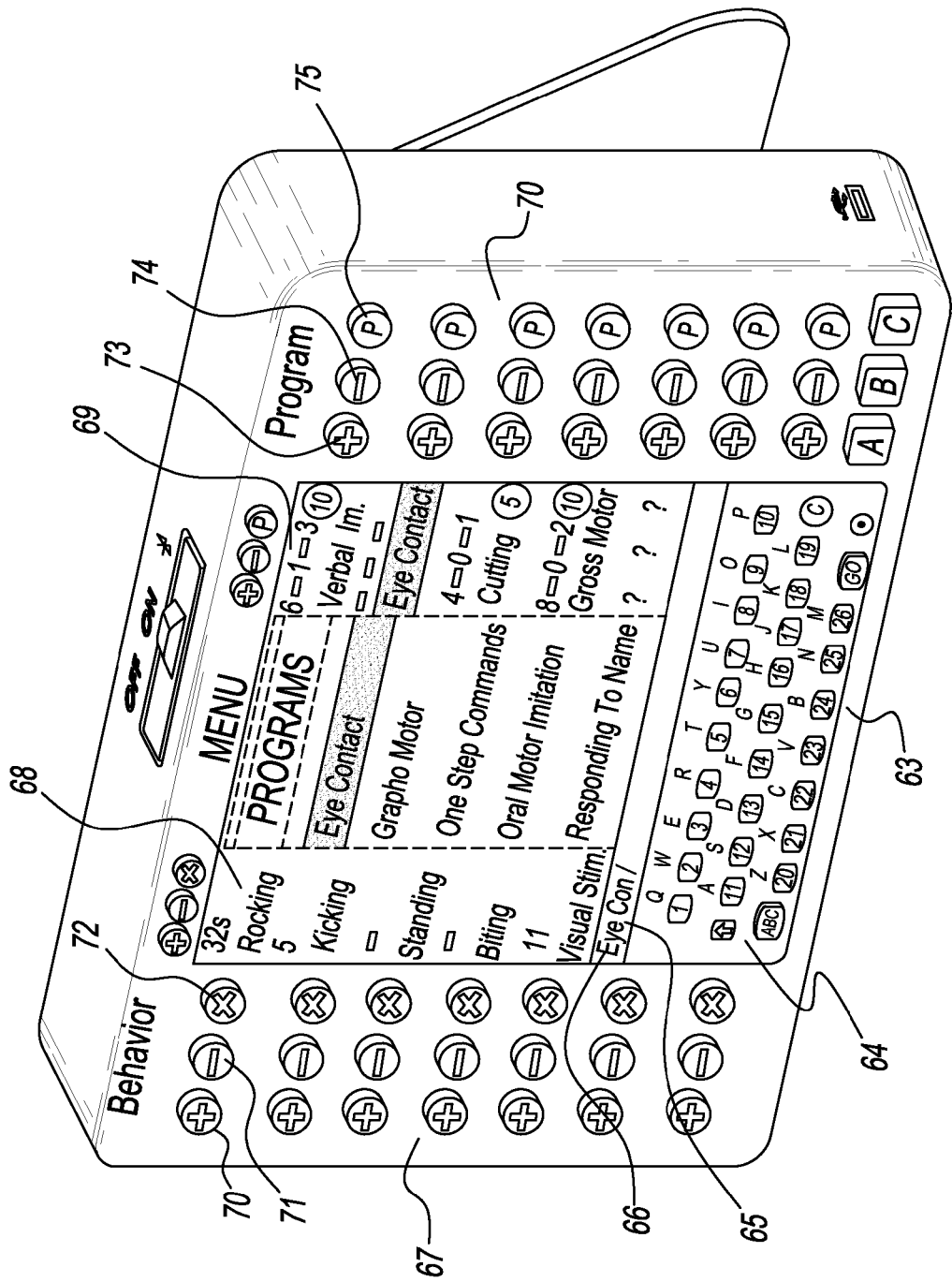
FIG. 3 illustrates a perspective view of an alternative embodiment of the present invention which incorporates a larger touchscreen to perform various functions.

More specifically, the invention is directed to a battery operated device for tracking behavioral data in the present invention, comprising: an information screen 16 on the face of the device displaying current behavior tracking data 4, 5, 7, 8, 13, 40, 49 as well as current program data 15, 16, 17, 18, 25, 35, 36, 37, 49 in one mode, a Menu 39 of behaviors and programs from which to choose in the Set mode 2, 24; displaying inputted anecdotal information regarding particular Antecedents 33, Behaviors 32 and Consequences 31 for targeted behaviors in another mode and reviewing previously inputted data in the Off mode;

a first group of buttons 44 on the same face of the device, labeled as integers 1-26 with a corresponding QWERTY keyboard accessed by pressing the ABC button 45 as well as a Shift button 46 represented by an upward arrow, a Clear button 33 and a Decimal point button 42, a Go button 43 to process information and a button with four-way directional arrows to scroll through information, wherein the first group of buttons are situated in one or more rows parallel to the longest dimension of the information screen;

Optionally, in an alternative embodiment, FIG. 3, this first group of buttons with numbers, a corresponding QWERTY keyboard and operational buttons 64 are contained 'virtually' in a larger information screen 63 on the face of the device, which can be accessed through finger movement swiped against the touchscreen 63.

Optionally, by swiping the screen in different directions, a user can highlight and select any Behavior, Program and Menu option and select it for any Behavior and Program in Set mode.

Optionally, in an alternative embodiment, FIG. 3, by swiping the screen, a user can highlight and select from the Menu any pre-programmed or manually inputted Antecedent, Behavior or Consequence anecdotal statements when in A, B and C are in their respective Set modes.

In FIG. 3, when in Set mode, which is accessed by holding down for three seconds the + buttons 9, 19 for behaviors and programs respectively and any one of the A, B, C buttons 31-33 to input anecdotal data, the user can also touch the bottom of the screen to show the virtual keyboard 64 and then can add new or access pre-programmed Behaviors, Programs or ABC data by typing them in the text box 66 above the keyboard 64.

All embodiments of the present invention device will be equipped to make suggestions for previously programmed or typed words as the user begins typing 65.

a second group of buttons 9-11, on the same face of the device, labeled as Behavior 12 wherein each of the four sets of buttons in the second group of buttons are placed in four rows perpendicular to the first group of buttons. Furthermore, included underneath each row of this group of buttons are sets of buttons/switches 1 indicating Set 2, Data 6 and Off 3 for each Behavior being monitored in various modes;

Optionally, in an alternative embodiment, FIG. 3, while the behavior and program data buttons 67 remain as they are in FIG. 1, the switches underneath each row of buttons has been removed. Instead, holding each of the data recording buttons (+, −, x and +, −, p) for three seconds accesses the setting, data taking and off modes respectively.

a third group of buttons 19-21 on the same face of the device, labeled as Programs wherein each of the four sets of buttons in the second group of buttons are placed in four rows perpendicular to the first group of buttons. Furthermore, included underneath each row of this group of buttons are a set of switches 1 indicating Set 2, Data 6 and Off 3 for each Program being monitored;

Optionally, in an alternative embodiment, FIG. 3, while the Program data buttons 70 remain as they are in FIG. 1, the switches underneath each row of buttons are removed.

Instead, holding each of the data recording buttons (+, − and x) for three seconds accesses the setting, data taking and off modes respectively.

a fourth group of buttons 31-33 on the same face of the device, labeled as A, B and C representing anecdotal data wherein this set of buttons is placed in one row parallel to the first group of buttons. Furthermore, included underneath this row of buttons is a switch 34 indicating Data and Off for recording Antecedents 33, Behaviors 32 and Consequences 31 for targeted behaviors being monitored;

Optionally, in an alternative embodiment, FIG. 3, while the A, B and C buttons 71 remain as they are in FIG. 1, the switches underneath each row of buttons are removed. Instead, holding each of the capital letter button (A, B or C) 71 for three seconds accesses the data taking buttons mode for each button respectively.

Optionally, in an alternative embodiment, FIG. 3, while the Behavior data buttons 67 remain as they are in FIG. 1, the switches underneath each row of buttons are removed. Instead, holding each of the data recording buttons for three seconds accesses the setting, data taking and off modes.

a fifth group of buttons 48 on the face or side of the device serving as scan buttons, wherein two scan or oppositional arrow buttons are arranged in one row which is parallel and two scan buttons are arranged in one column which is perpendicular to the first group of buttons;

an On, Off and wireless switch/button 14 on the face or side of the device with the wireless position 50 accessing wireless data transfer;

an SD card port 29 on the side or face of the device; and a USB port 30 on a side of the device serving for data transfer.

Referring to FIG. 1, one of the primary functions of the buttons and switches on the left face of the device is to record data regarding different Behaviors 7, 4, 40. This information corresponds to the data displayed on the left side of the device's screen demarcated by a vertical dotted line. Each row denotes a different behavior and unlimited behaviors can be added by using the directional scanning buttons to scroll up or down to a blank space indicated by three question marks as illustrated in the middle of the right side of the screen in FIG. 3. The user would by scrolling would line the row of question marks up with a switch that is put in the Set position 2. Next the user can manually type in the name of the behavior or by moving the multi-directional scanning or scrolling button 48 to the right can alternatively choose a selection from a pre-programmed list of Behaviors in the Menu section 39 which is demarcated by dotted vertical lines in the middle of the information screen. By using the scanning button 48 to scroll up and down through pre-programmed behavior or program choices, as depicted by the highlighted word Eye Contact 36 displayed in the upper middle portion of the information screen in FIG. 1, the user can select a particular one by pressing the Go button 43 on the keyboard 44. The selected behavior 40 will then appear in highlighted form in place of the three question marks and the user can slide the switch to the Data position 6 to begin taking data on that particular behavior which would turn the dash mark 49 denoting no data to a number 5. By pressing the + button, the user not only begins a count 5 for a particular behavior but also begins an internal timer which records the time each incidence of that behavior occurs. Once this information is transferred, via USB, SD card or wireless transmission including but not limited to Bluetooth or WiFi, it can be organized in multiple graphic formats 59, 62 such as count, rate and celeration to name a few examples depicted in FIG. 2.

To collect data for certain temporally-related formats 60, 61 that require timing 60 and time sampling 61 data, the user must first choose which type of data they wish to collect before they begin recording. This can be done when the Behavior 12 switch is still in the Set position 2 and the chosen behavior is still highlighted. At this point, the user can press the Go button 43 to scroll through menus of data collection categories including by not limited to Event Recording, Timing and Time Sampling and by pressing the Go button 43 on any particular category will then be directed to sub-categories of options within those categories including but not limited to Celeration, Duration, Interresponse Time, Response Latency, Whole Interval Recording, Partial Interval Recording and Momentary Time Sampling. To make a selection or multiple selections, the user will scroll through options and by doing so highlighting them. Once an option is highlighted the user will press the Go button 43 to select it. The user can use the directional scanning button 48 to highlight and select multiple formats. Once the method or methods of data collection are chosen, the user can press the + 9 and − 10 buttons as illustrated in FIG. 1 to respectively start and stop the timer and press the x 11 button to indicate an incidence of a behavior within the time period being examined. For interval recording, the running time 8 will blink at the interval the user has programmed to remind the user to record the occurrence by pressing the x button or absence of a behavior by not pressing any button. The method of data collection 56 can also be programmed on an external computing device such as a laptop 52 as depicted in FIG. 2 and subsequently transferred to the present invention via wireless 52 or another chosen method of transmission.

Just as in recording behavior data, the user can record program data 16 in a similar manner. Referring to FIG. 1, one of the primary functions of the buttons and switches on the right face of the device is to record data regarding different Programs 19. This information corresponds to the data displayed on the right side of the device's screen demarcated by a vertical dotted line. Each row denotes a different program and unlimited programs can be added by using the directional scanning button 48 to scroll up or down to a blank space indicated by three question marks as illustrated in the middle of the right side of the information screen of the device in FIG. 3. Referring to FIG. 1 again, the user would line the row of question marks up with a switch that is placed in the Set position 23. In the preferred embodiment, the user can manually type in the name of a program by simply typing on the keyboard 44 or by moving the multi-directional scanning/scrolling button 48 to the left or can alternatively choose a selection from a pre-programmed list of Programs in the Menu section 39 which is demarcated by vertical dotted lines in the middle of the information screen. By using the scanning button 48 to scroll up and down through pre-programmed program choices, as depicted by the highlighted word Eye Contact 38 displayed in the upper middle portion of the information screen in FIG. 1, the user can select that particular program 23 by pressing the Go button 43 on the keyboard 44. The selected program 23 will then appear in highlighted form in place of the three question marks and the user can slide the switch to the Data position 26 to begin taking data for that particular program which would turn the three dash marks 49 above the program name, indicating that no data has been recorded yet for this program, to a number in one of three spots, 35-37. By pressing the + button 19, the user will indicate the student answered correctly 37, by pressing the − button 20, the user will indicate that the student answered incorrectly 36 and by pressing the P 21 button, the user will indicate that the student needed to be prompted 35 to answer.

The encircled number 10 next to each program name will indicate the running tally of opportunities that student had to answer thus far. Optionally, the keyboard will be illuminated 47 to indicate the number of trials completed in that program to that point.

Figure 2:
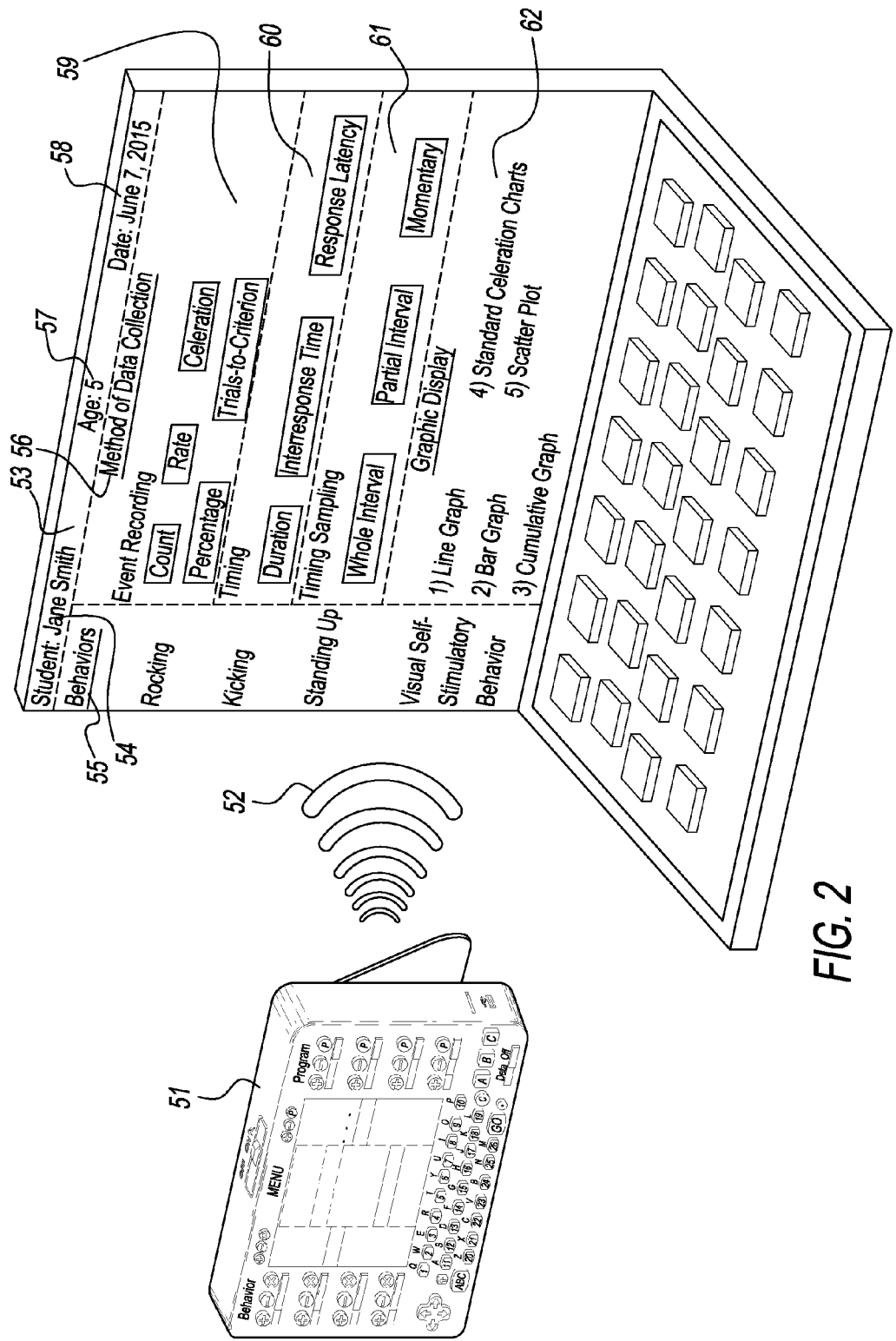
FIG. 2 illustrates a representation of the downloading function of the present invention.

Just as with behaviors, once this program data is transferred and synched to a personal computing device, main computer or information cloud, via USB 30, SD card 29 or wireless transmission 52 (FIG. 2) including but not limited to Bluetooth 50 (FIG. 1) or WiFi, it can be organized in multiple graphic formats 59, 62 such as count, rate and celeration to name a few examples depicted in FIG. 2.

Like with behaviors, the method of data collection 56 and graphic display format 62 for programs can also be predetermined on an external computing device such as a laptop 52 as depicted in FIG. 2 and subsequently transferred to the present invention via wireless 52 or another method of transmission.

The preferred embodiment of the device also comprises a communication means to interface with an external computing device, with this external computing device being capable of viewing and extracting information from the device as well as sending information to the device in the present invention. In one example, the device further comprises Bluetooth and WiFi abilities 52 (FIG. 2) and can be synchronized with the personal computing devices or other computing/information storage devices such as main computer terminals and information clouds.

Optionally, the device can further be tracked for its location.

Optionally, in alternative embodiments, the device comprises a touchpad or touchscreen 63 as in FIG. 3 to input and access data comprising of additional rows of buttons 67, 70, a larger screen 63 to display more programs and behaviors, a virtual keyboard and text box 65 where the user can type behavior and program 66 names as well as anecdotal information for ABC data recording and by holding each of the +, − and x behavior buttons, 70-72 for behaviors and the +, − and P program buttons 73-75 and the A, B, C anecdotal data buttons for three seconds, respectively accesses Set, Data and Off modes. Also, in an alternative embodiment, if the A, B, C anecdotal data buttons in the lower right corner of the face of the device as illustrated in FIG. 3 are each pressed for three seconds, they will access the data taking mode for anecdotal Antecedent, Behavior and Consequence data recording modes respectively.

Optionally, the device comprises a video screen and/or audio monitoring system capable of recording wireless transmission of images and audio from a camera and/or audio receiver.

Intrinsically, an operable device described in the present invention requires a microprocessor to compile the information input and store in a temporary storage for further data transfer or manipulating. The microprocessor may comprise a microcontroller to respond when a different operation mode, behavior-related button is selected and a memory storage to communicate with the microcontroller and/or external device.

The device can be made in different shapes, with ergonomic features or easy to grab onto features. Preferably, as illustrated in FIG. 1, the device is rectangular in shape.

The device is intended to have maximum portability. In one example, the device has a durable metal and/or plastic clip on the back, which the caregiver can adjust to prop up the device on a table or flat surface. In another example, the caregiver can wear the device on her belt/pants. In another, a comfortable cord/fabric is fastened to the device so that it can be worn around a caregiver's neck to maximize portability.

In accordance with the present invention, the device is battery operated. Optionally, the device's battery has a plug-in rechargeable function to enable quicker recharge if a battery replacement or recharge is not immediately available.

Preferably, the device is also lightweight.

I claim:

1. A battery operated multi-event data and time tracking device for monitoring behaviors and behavior-related data consisting essentially of:
    a first plurality of buttons on the face the device, grouped together and labeled with numbers 1-26 and letters A-Z organized in a QWERTY format, which records and stores behavior-related data and has the capability of instantly indicating that data as well as an aggregate number of instances of a particular behavioral event or program through display on an information screen on the face of the device;
    a second plurality of buttons on the face of the device, grouped together and labeled to represent their functions, wherein each button accesses and has a capability of recording data of different behavioral events and programs with all buttons corresponding to representation in iconic, numerical or word form on the information screen of the device;
    a clear button, a decimal point button and scanning multi-directional arrow button on the face of the device with a capability to navigate different screens of the device through finger movements on the face of the device;
    an On, Off and Wireless transmission switch on a side of the device;
    an information screen on the face of the device displaying temporal, numerical and anecdotal data in various modes with respect to particular events and programs,
    a microprocessor for providing temporary memory storage for the device and mode selection and data input for each of the buttons as well as allowing wireless, WiFi, and/or Bluetooth transmission of data to and from a permanent memory storage of other computing devices and/or data cloud; and
    USB and SD card ports on a side of the device for optional non-wireless data transfer from the temporary memory storage to and from the permanent memory storage for the purpose of having the data organized in a graphic format to facilitate a functional analysis of behaviors as well as a comparison of behavior trends based on the frequency, duration, temporal data and simultaneous occurrences of behaviors.

2. A battery operated multi-event data and time tracking device for monitoring behaviors and behavior-related data consisting essentially of:
    a first plurality of virtual buttons on an information touch screen of the device, grouped together and labeled with numbers and letters organized in a QWERTY format, which records and stores behavior-related data and has the capability of instantly indicating that data as well as an aggregate number of instances of a particular behavioral event or program through display on the information touch screen on the face of the device;
    a second plurality of buttons on the face of the device, grouped together and labeled to represent their functions, wherein each button accesses and has a capability of recording data of different behavioral events and programs with all buttons corresponding to representation in iconic, numerical or word form on the information touch screen of the device;
    a clear button, a decimal point button and scanning multi-directional arrow button on the information touch screen with a capability to navigate different screens of the device through finger movements on said information touch screen;
an On, Off and Wireless transmission switch on a side of the device;
an information touch screen on the face of the device displaying temporal, numerical and anecdotal data in various modes with respect to particular events and programs, including a virtual keyboard to navigate through the information touch screen,
a microprocessor for providing temporary memory storage for the device and mode selection and data input for each of the buttons as well as allowing wireless, WiFi, and/or Bluetooth transmission of data to and from a permanent memory storage of other computing devices and/or data cloud; and
USB and SD card ports on a side of the device for optional non-wireless data transfer from the temporary memory storage to and from the permanent memory storage for the purpose of having the data organized in a graphic format to facilitate a functional analysis of behaviors as well as a comparison of behavior trends based on the frequency, duration, temporal data and simultaneous occurrences of behaviors.

3. The device of claim 1 or claim 2, wherein it has dimensions of a hand-held device to facilitate portability.

4. The device of claim 1 or claim 2, wherein it has a durable metal and/or plastic clip on the back thereof so it can adjusted to be propped up on table or other flat surface.

5. The device of claim 1 or claim 2, wherein it has a durable metal and/or plastic clip on the back thereof so it can adjusted to be worn on a belt/pant or worn.

6. The device of claim 1 or claim 2, wherein it has a durable metal and/or plastic clip on the back thereof so it can be adjusted to be fastened to a comfortable cord or loop allowing it be worn around the neck or wrist.

* * * * *